United States Patent
Srinivasan et al.

(10) Patent No.: US 10,865,217 B2
(45) Date of Patent: Dec. 15, 2020

(54) PROCESS FOR THE PREPARATION OF 5-(4-CYANOPHENOXY)-1,3-DIHYDRO-1-HYDROXY-[2,1]-BENZOXABOROLE AND POLYMORPHS THEREOF

(71) Applicants: MSN LABORATORIES PRIVATE LIMITED, R&D CENTER, Hyderabad (IN); Thirumalai Rajan Srinivasan, Hyderabad (IN)

(72) Inventors: Thirumalai Rajan Srinivasan, Hyderabad (IN); Eswaraiah Sajja, Hyderabad (IN); Venkat Reddy Ghojala, Hyderabad (IN); Markandeya Bekkam, Hyderabad (IN)

(73) Assignee: MSN LABORATORIES PRIVATE LIMITED, R & D CENTER, Hyderabad (IN)

( * ) Notice: Subject to any disclaimer, the term of this patent is extended or adjusted under 35 U.S.C. 154(b) by 0 days.

(21) Appl. No.: 16/616,030

(22) PCT Filed: May 23, 2018

(86) PCT No.: PCT/IN2018/050328
§ 371 (c)(1),
(2) Date: Nov. 22, 2019

(87) PCT Pub. No.: WO2018/216032
PCT Pub. Date: Nov. 29, 2018

(65) Prior Publication Data
US 2020/0190120 A1 Jun. 18, 2020

(30) Foreign Application Priority Data
May 23, 2017 (IN) .............................. 201741018145

(51) Int. Cl.
C07F 5/02 (2006.01)

(52) U.S. Cl.
CPC .......... *C07F 5/027* (2013.01); *C07B 2200/13* (2013.01)

(58) Field of Classification Search
CPC .................................................. C07B 2200/13
See application file for complete search history.

(56) References Cited

U.S. PATENT DOCUMENTS 8,039,451 B2   10/2011   Baker et al.

FOREIGN PATENT DOCUMENTS

WO   WO 2009/111676   9/2009

OTHER PUBLICATIONS

Tsumotu Akama et al., Discovery and structure . . . of 6-(benzoylamino)benzoxaboroles . . . anti-inflammatory agents, Bioorganic and Medicinal Chem. 23 (2013) 5870-5873.
International Search Report dated Sep. 20, 2018.
Written Opinion of the International Searching Authority dated Sep. 20, 2018.

*Primary Examiner* — Timothy R Rozof
(74) *Attorney, Agent, or Firm* — IP Pundit LLC

(57) ABSTRACT

The present invention relates to process for the preparation of 5-(4-cyano phenoxy)-1,3-dihydro-1-hydroxy-[2,1]-benzoxaborole represented by the following structural formula-1 and polymorphs thereof. The present invention also relates to salts of 5-(4-cyano phenoxy)-1,3-dihydro-1-hydroxy-[2,1]-benzoxaborole and process for their preparation and their use in the preparation of pure compound of the formula-1.

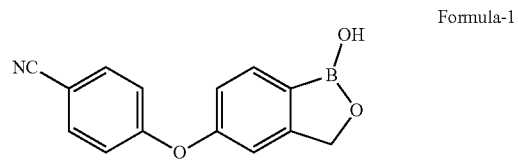

Formula-1

10 Claims, 3 Drawing Sheets

PROCESS FOR THE PREPARATION OF 5-(4-CYANOPHENOXY)-1,3-DIHYDRO-1-HYDROXY-[2,1]-BENZOXABOROLE AND POLYMORPHS THEREOF

RELATED APPLICATION

This application claims the benefit of priority of our Indian patent application 201741018145 filed on May 23, 2017 which is incorporated herein as reference.

FIELD OF THE INVENTION

The present invention provides process for the preparation of 5-(4-cyanophenoxy)-1,3-dihydro-1-hydroxy-[2,1]-benzoxaborole represented by the following structural formula-1 and polymorphs thereof.

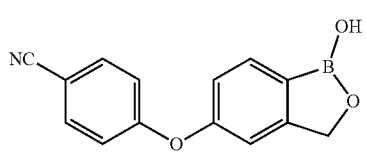

Formula-1

The present invention also provides solid state forms of compound of formula-1 and process for preparation thereof.

BACKGROUND OF THE INVENTION 5-(4-Cyanophenoxy)-1,3-dihydro-1-hydroxy-[2,1]-benzoxaborole (commonly known as Crisaborole) is a phosphodiesterase-4 inhibitor. Crisaborole is approved by US FDA on Dec. 14, 2016 and sold under the brand name EUCRISA which is indicated for the topical treatment of mild to moderate atopic dermatitis in patients 2 years of age and older. This compound is under clinical trials for the treatment of psoriasis.

U.S. Pat. No. 8,039,451B2 (herein after referred as U.S. Pat. No. '451 patent) first discloses 5-(4-cyanophenoxy)-1,3-dihydro-1-hydroxy-[2,1]-benzoxaborole, its analogs and process for preparation thereof.

U.S. Pat. No. '451 patent has disclosed a process for the preparation of Crisaborole in example-4, compound-4.2.q. The process disclosed in the said patent suffers from several disadvantages which includes utilization of flash column chromatography to purify the product which is a cumbersome, expensive and time consuming technique. Further the product is obtained in very low yield and has only 80% purity even after column purification. Hence, one or more purification steps are required to purify the obtained compound in order to comply with various regulatory requirements. These lengthy purification procedures will greatly reduce the yield of the product and there by increases the overall cost of the production. Hence, this process is not suitable to adopt it on commercial scale.

In view of all these drawbacks associated with the prior-art procedure, there is a significant need in the art to develop an improved process for the preparation of Crisaborole.

Further, the U.S. Pat. No. '451 patent did not provide any information on the polymorphic form of the compound obtained by the process described therein.

Discovery and development of various polymorphic forms of an active pharmaceutical ingredient provides the formulation scientist with the opportunity to select the more suitable polymorph to prepare the finished product.

Hence, there is a significant need in the art to develop various polymorphic forms of the said compound to select the highly stable as well as more bioavailable polymorph to prepare the finished product.

The present inventors have earnestly tried to develop solid state forms of 5-(4-cyanophenoxy)-1,3-dihydro-1-hydroxy-[2,1]-benzoxaborole. After numerous trials and many efforts the present inventors have surprisingly found various polymorphic forms of the said compound which are described in the present invention.

BRIEF DESCRIPTION OF THE INVENTION

The first aspect of the present invention is to provide a process for the preparation of 5-(4-cyanophenoxy)-1,3-dihydro-1-hydroxy-[2,1]-benzoxaborole compound of formula-1.

The second aspect of the present invention is to provide a process for the preparation of 2-halo-5-hydroxybenzyl acetate compound of general formula-4.

The third aspect of the present invention is to provide a process for the preparation of 2-halo-5-(4-cyanophenoxy) benzyl acetate compound of general formula-6.

The fourth aspect of the present invention is to provide a process for the preparation of compound of formula-1.

The fifth aspect of the present invention is to provide organic amine salts of compound of formula-1.

The sixth aspect of the present invention is to provide a process for the preparation of organic amine salts of compound of formula-1.

The seventh aspect of the present invention is to provide a process for the purification of compound of formula-1.

The eighth aspect of the present invention is to provide a process for the preparation of crystalline form-2 of compound of formula-1.

An embodiment of the present invention is to provide novel crystalline polymorphs of compound of formula-1 and processes for their preparation.

BRIEF DESCRIPTION OF THE DRAWING

FIG. 1: Illustrates the powder X-Ray diffraction (PXRD) pattern of 2-bromo-5-(4-cyanophenoxy)benzyl acetate compound of formula-6a.

DETAILED DESCRIPTION OF THE INVENTION

Figure 1:
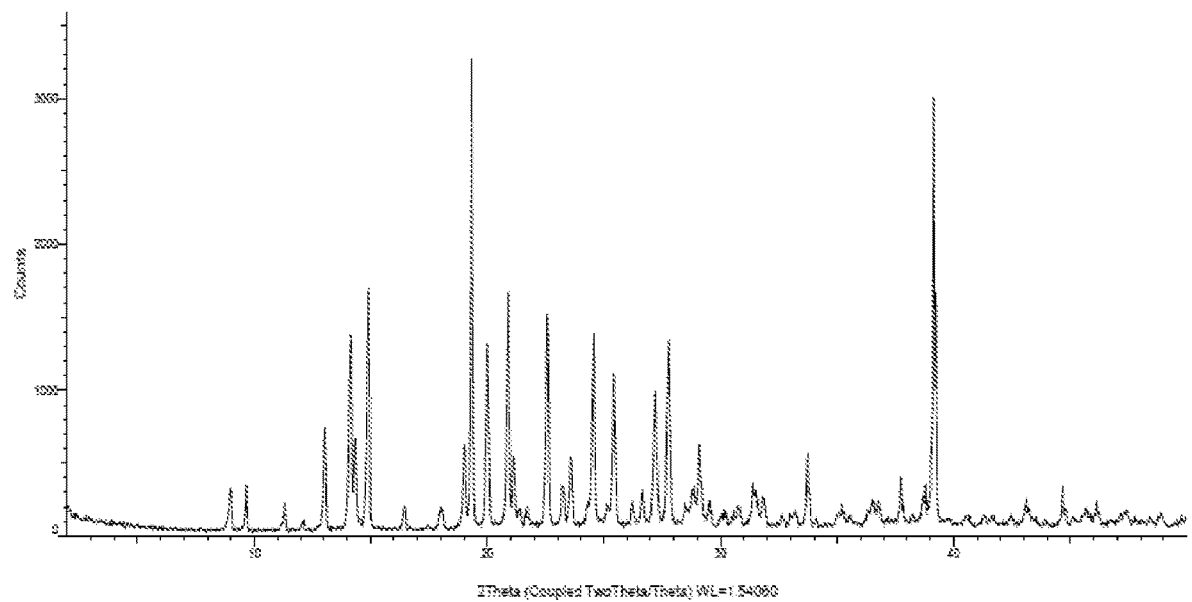

The "suitable solvent" used in the present invention can be selected from but not limited to "hydrocarbon solvents" such as n-pentane, n-hexane, n-heptane, cyclohexane, petroleum ether, benzene, toluene, xylene and the like; "ether solvents" such as dimethyl ether, diethyl ether, diisopropyl ether, methyl tert-butyl ether, 1,2-dimethoxyethane, tetrahydrofuran, 1,4-dioxane and the like; "ester solvents" such as methyl acetate, ethyl acetate, n-propyl acetate, isopropyl acetate, n-butyl acetate, isobutyl acetate, tert-butyl acetate and the like; "polar-aprotic solvents" such as dimethylacetamide, dimethylformamide, dimethylsulfoxide, N-methylpyrrolidone (NMP) and the like; "chloro solvents" such as dichloromethane, dichloroethane, chloroform, carbon tetrachloride and the like; "ketone solvents" such as acetone, methyl ethyl ketone, methyl isobutyl ketone and the like; "nitrile solvents" such as acetonitrile, propionitrile, isobutyronitrile and the like; "alcohol solvents" such as methanol, ethanol, n-propanol, iso-propanol, n-butanol, iso-butanol, 2-butanol, tert-butanol, ethane-1,2-diol, propane-1,2-diol and the like; "polar solvents" such as water; carboxylic acid solvents such as formic acid, acetic acid and the like or mixture of any of the aforementioned solvents.

The "suitable base" used in the present invention can be selected from but not limited to "inorganic bases" selected from "alkali metal carbonates" such as sodium carbonate, potassium carbonate, lithium carbonate, cesium carbonate and the like; "alkali metal bicarbonates" such as sodium bicarbonate, potassium bicarbonate, lithium bicarbonate, cesium bicarbonate and the like; "alkali metal hydroxides" such as sodium hydroxide, potassium hydroxide, lithium hydroxide, cesium hydroxide and the like; "alkali metal hydrides" such as sodium hydride, potassium hydride, lithium hydride and the like; "alkali metal amides" such as sodium amide, potassium amide, lithium amide and the like; ammonia; "organic bases" like "alkali metal alkoxides" such as sodium methoxide, sodium ethoxide, potassium methoxide, potassium ethoxide, lithium methoxide, lithium ethoxide, sodium tert.butoxide, potassium tert.butoxide, lithium tert.butoxide and the like; alkali metal and alkali earth metal salts of acetic acid such as sodium acetate, potassium acetate, magnesium acetate, calcium acetate and the like; dimethylamine, diethylamine, diisopropyl mine, diisopropylethylamine (DIPEA), diisobutylamine, triethylamine, triisopropyl amine, tributylamine, tert.butyl amine, pyridine, piperidine, 4-dimethylaminopyridine (DMAP), quinoline, imidazole, N-methylimidazole, 1,8-diazabicyclo[5.4.0]undec-7-ene (DBU), 1,5-diazabicyclo[4.3.0]non-5-ene (DBN), dimethylaniline, N-methylmorpholine (NMM), 1,4-diazabicyclo[2.2.2]octane (DABCO), 2,6-lutidine and the like; "organolithium bases" such as methyl lithium, n-butyl lithium, lithium diisopropylamide (LDA) and the like; "organosilicon bases" such as lithium hexamethyldisilazide (LiHMDS), sodium hexamethyldisilazide (NaHMDS), potassium hexamethyldisilazide (KHMDS) and the like or their mixtures.

The first aspect of the present invention provides a process for the preparation of 5-(4-cyanophenoxy)-1,3-dihydro-1-hydroxy-[2,1]-benzoxaborole compound of formula-1, comprising of;
a) reduction of 2-halo-5-hydroxybenzaldehyde compound of general formula-2

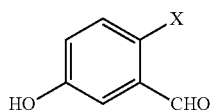

Formula-2 wherein, 'X' represents halogens such as F, Cl, Br & I;
with a suitable reducing agent in a suitable solvent to provide 4-halo-3-(hydroxymethyl) phenol compound of general formula-3,

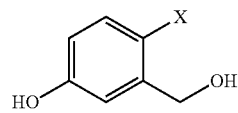

Formula-3 b) reacting the compound of general formula-3 with a suitable acetylating agent optionally in presence of a suitable base in a suitable solvent to provide 2-halo-5-hydroxybenzyl acetate compound of general formula-4,

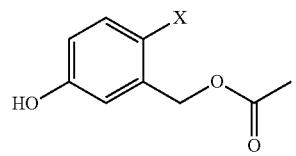

Formula-4 c) reacting the compound of general formula-4 with 4-halobenzonitrile compound of general formula-5

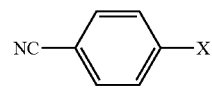

Formula-5 wherein, 'X' represents halogens such as F, Cl, Br & I;
in presence of a suitable base in a suitable solvent to provide 2-halo-5-(4-cyanophenoxy)benzyl acetate compound of general formula-6,

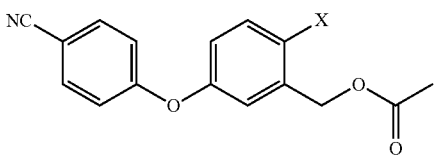

Formula-6 d) reacting the compound of general formula-6 with bis (pinacolato)diboron compound having the following formula

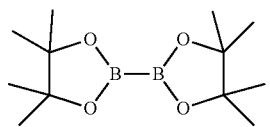

in presence of a suitable palladium catalyst and a suitable base in a suitable solvent to provide 5-(4-cyanophenoxy)-2-(4,4,5,5-tetramethyl-1,3,2-dioxaborolan-2-yl)benzyl acetate compound of formula-7,

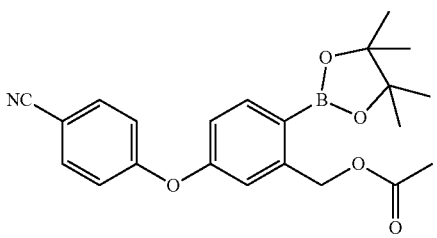

Formula-7 e) treating the compound of formula-7 with a suitable acid optionally in presence of a suitable solvent to provide compound of formula-1, f) purifying the compound of formula-1 from a suitable solvent or mixture of solvents to provide pure compound of formula-1.

Wherein, in step-a) the suitable reducing agent is selected from but not limited to sodium borohydride, sodium borohydride in combination with $BF_3$.etherate, sodium cyanoborohydride, sodium triacetoxy borohydride, lithium aluminium hydride, lithium borohydride, Red-Al, borane, $BH_3$-tetrahydrofuran, $BH_3$-dimethyl sulfide and the like.

In step-b) the suitable acetylating agent is selected from but not limited to acetic anhydride, acetyl chloride, acetic acid or mixtures thereof and the suitable base is selected from organic bases.

In step-c) the suitable base is selected from inorganic bases, organic bases or mixtures thereof.

In step-d) the suitable palladium catalyst is selected from but not limited to palladium(II) acetate, palladium(II) acetoacetonate, palladium chloride ($PdCl_2$), tetrakis(triphenylphosphine)palladium, dichlorobis(triphenylphosphine)palladium, [1,1'-bis(diphenylphosphino)ferrocene]dichloro palladium(II) [Pd(dppf)$Cl_2$], combinations thereof and the like; and the reaction can be carried out optionally in presence of a suitable ligand such as triphenylphosphine, tri(o-tolyl)phosphine, tricyclohexylphosphine combinations thereof and the like, the suitable base is selected from inorganic bases, organic bases or mixtures thereof.

In step-e) the suitable acid is preferably hydrochloric acid.

In step-a) to step-f) the suitable solvent wherever necessary is selected from hydrocarbon solvents, ether solvents, ester solvents, polar-aprotic solvents, chloro solvents, ketone solvents, nitrile solvents, alcohol solvents, polar solvents and the like or mixtures thereof.

In one embodiment of the present invention, the compound of formula-7 can be treated with a suitable acid preferably with hydrochloric acid to directly provide compound of formula-1.

In another embodiment of the present invention, the compound of formula-7 is first treated with a suitable base selected from alkali metal hydroxides, alkali metal carbonates, alkali metal alkoxides and alkali metal bicarbonates to provide the hydroxy compound having the following formula which is then treated with a suitable acid such as hydrochloric acid to provide compound of formula-1.

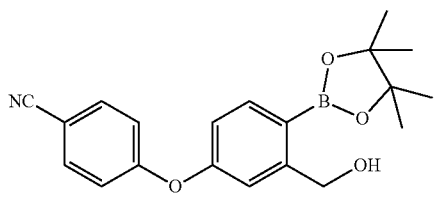 [SMILES: CC1(C)OB(c2ccc(Oc3ccc(C#N)cc3)cc2CO)OC1(C)C]

U.S. Pat. No. 8,039,450B2 generically discloses the hydrolysis of compound of formula-7 in presence of sodium hydroxide to cleave the acetyl group and to provide corresponding hydroxy intermediate compound which is then treated with suitable acid such as hydrochloric acid to provide compound of formula-1.

The present inventors have developed a one-step process for the conversion of compound of formula-7 to compound of formula-1 which involves the addition of hydrochloric acid to compound of formula-7 and heating the reaction mixture to a temperature of 85-90 deg C. to directly provide the compound of formula-1.

This one-step process is simple and avoids multiple operations and work up procedures for the said conversion. Hence, it is advantageous over the prior-art process.

The process developed by the present inventors is simple, safe, ecofriendly and commercially viable and involves the usage of simple and commercially available raw materials, reagents and solvents.

A preferred embodiment of the present invention provides a process for the preparation of compound of formula-1, comprising of;

a) reduction of 2-bromo-5-hydroxybenzaldehyde compound of formula-2a

Formula-2a

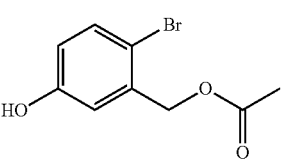

with sodium borohydride in tetrahydrofuran to provide 4-bromo-3-(hydroxymethyl) phenol compound of formula-3a, Formula-3a b) reacting the compound of formula-3a with acetic anhydride in presence of triethylamine in ethyl acetate to provide 2-bromo-5-hydroxybenzyl acetate compound of formula-4a, Formula-4a c) reacting the compound of formula-4a with 4-fluorobenzonitrile compound of formula-5a Formula-5a

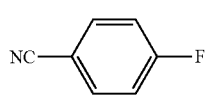

in presence of potassium carbonate in dimethylsulfoxide to provide 2-bromo-5-(4-cyanophenoxy)benzyl acetate compound of formula-6a, Formula-6a

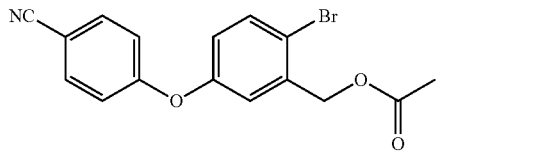

d) reacting the compound of formula-6a with bis(pinacolato) diboron compound having the following formula

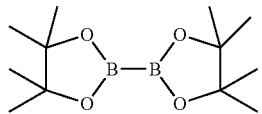

in presence of Pd(dppf)Cl$_2$ and potassium acetate in 1,4-dioxane to provide 5-(4-cyanophenoxy)-2-(4,4,5,5-tetramethyl-1,3,2-dioxaborolan-2-yl)benzyl acetate compound of formula-7, Formula-7

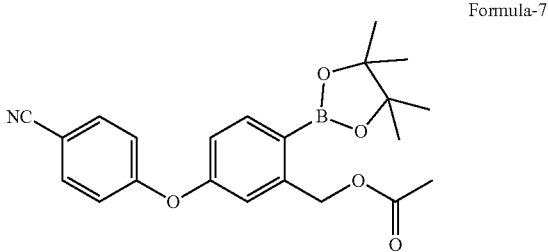 [SMILES: CC(=O)OCc1cc(Oc2ccc(C#N)cc2)ccc1B1OC(C)(C)C(C)(C)O1]

e) treating the compound of formula-7 with hydrochloric acid in water to provide compound of formula-1,
f) purifying the compound of formula-1 by dissolving it in methanol or in a mixture of dimethylsulfoxide and methanol and combining the obtained solution with water to precipitate pure compound of formula-1.

The process for the preparation of compound of formula-1 developed by the present inventors produces highly pure compound of formula-1 with excellent yield. All the related substances and residual solvents are controlled well within the limits as suggested by ICH guidelines and most of the related substances are controlled in non-detectable levels.

The compound of formula-1 produced by various processes of the present invention is having purity of greater than 99%, preferably greater than 99.5%, more preferably greater than 99.7%, most preferably greater than 99.9% by HPLC.

The 2-bromo-5-hydroxybenzaldehyde compound of formula-2a and 4-fluoro benzonitrile compound of formula-5a which are utilized in the above process can be prepared by any of the processes known in the art or they can be procured from any commercial sources available.

The second aspect of the present invention provides a process for the preparation of 2-halo-5-hydroxybenzyl acetate compound of general formula-4, comprising of reacting the 4-halo-3-(hydroxymethyl)phenol compound of general formula-3 with a suitable acetylating agent optionally in presence of a suitable base in a suitable solvent to provide compound of general formula-4.

Wherein, the suitable acetylating agent is selected from but not limited to acetic anhydride, acetyl chloride, acetic acid or mixtures thereof and the suitable base is selected from organic bases.

The suitable solvent is selected from hydrocarbon solvents, ether solvents, ester solvents, polar-aprotic solvents, chloro solvents, ketone solvents, nitrile solvents, alcohol solvents, polar solvents and the like or mixtures thereof.

A preferred embodiment of the present invention provides a process for the preparation of 2-bromo-5-hydroxybenzyl acetate compound of formula-4a, comprising of reacting the 4-bromo-3-(hydroxymethyl) phenol compound of formula-3a with acetic anhydride in presence of triethylamine in ethyl acetate to provide compound of formula-4a.

The third aspect of the present invention provides a process for the preparation of 2-halo-5-(4-cyanophenoxy) benzyl acetate compound of general formula-6, comprising of reacting the 2-halo-5-hydroxybenzyl acetate compound of general formula-4 with 4-halobenzonitrile compound of general formula-5 in presence of a suitable base in a suitable solvent to provide compound of general formula-6.

Wherein, the suitable base is selected from inorganic bases, organic bases or mixtures thereof and the suitable solvent is selected from hydrocarbon solvents, ether solvents, ester solvents, polar-aprotic solvents, chloro solvents, ketone solvents, nitrile solvents, alcohol solvents, polar solvents and the like or mixtures thereof.

A preferred embodiment of the present invention provides a process for the preparation of 2-bromo-5-(4-cyanophenoxy)benzyl acetate compound of formula-6a, comprising of reacting the 2-bromo-5-hydroxybenzyl acetate compound of formula-4a with 4-fluorobenzonitrile compound of formula-5a in presence of potassium carbonate in dimethylsulfoxide to provide compound of formula-6a.

An embodiment of the present invention provides 2-bromo-5-(4-cyanophenoxy) benzyl acetate compound of formula-6a as a crystalline solid.

The other embodiment of the present invention provides crystalline polymorph of compound of formula-6a characterized by its PXRD pattern having peaks at 13.0, 14.1, 14.9, 19.3, 20.0, 20.7, 22.5, 24.5, 25.4, 27.2, 27.7±0.2° of 2-theta values.

In one embodiment, the said crystalline polymorph is characterized by its PXRD pattern as illustrated in FIG. 1.

The fourth aspect of the present invention provides a process for the preparation of compound of formula-1, comprising of;
a) reacting the 2-halo-5-(4-cyanophenoxy)benzyl acetate compound of general formula-6 with bis(pinacolato)diboron in presence of a suitable palladium catalyst and a suitable base in a suitable solvent to provide 5-(4-cyanophenoxy)-2-(4,4,5,5-tetramethyl-1,3,2-dioxaborolan-2-yl)benzyl acetate compound of formula-7,
b) treating the compound of formula-7 with a suitable acid optionally in presence of a suitable solvent to provide compound of formula-1.

Wherein, in step-a) the suitable palladium catalyst is selected from palladium(II) acetate, palladium(II) acetoacetonate, palladium chloride (PdCl$_2$), tetrakis(triphenylphosphine)palladium, dichlorobis(triphenylphosphine)palladium, [1,1'-bis(diphenylphosphino)ferrocene]dichloro palladium(II) [Pd(dppf)Cl$_2$], combinations thereof and the like; and the reaction can be carried out optionally in presence of a suitable ligand such as triphenylphosphine, tri(o-tolyl)phosphine, tricyclohexylphosphine combinations thereof. The suitable base is selected from inorganic bases, organic bases or mixtures thereof.

In step-b) the suitable acid is preferably hydrochloric acid.

In step-a) and step-b) the suitable solvent wherever necessary is selected from hydrocarbon solvents, ether solvents, ester solvents, polar-aprotic solvents, chloro solvents, ketone solvents, nitrile solvents, alcohol solvents, polar solvents and the like or mixtures thereof.

A preferred embodiment of the present invention provides a process for the preparation of compound of formula-1, comprising of;
a) reacting the 2-bromo-5-(4-cyanophenoxy)benzyl acetate compound of formula-6a with bis(pinacolato)diboron in presence of Pd(dppf)Cl$_2$ and potassium acetate in 1,4-dioxane to provide compound of formula-7,
b) treating the compound of formula-7 with hydrochloric acid in water to provide compound of formula-1.

The fifth aspect of the present invention provides organic amine salts of compound of formula-1. Wherein, the "organic amine" is selected from but not limited to methyl amine, ethyl amine, n-propyl amine, isopropyl amine, n-butyl amine, iso-butyl amine, tertiary butyl amine, octyl amine, 2-ethyl hexylamine, benzyl amine, α-methyl-benzylamine, phenyl ethylamine, dibenzylamine, N-methylbenzylamine, N,N-dimethylbenzylamine, N,N-diethyl benzyl amine, N-ethyl-N-methylbenzylamine, tribenzyl amine, cyclopentylamine, cyclohexyl amine, cycloheptylamine, N-methylcyclopentylamine, N-ethylcyclohexyl amine, N-ethyl cycloheptylamine, dicyclohexyl amine, N,N-dimethylcyclo pentylamine, N,N-dimethyl cyclohexylamine, N,N-diethylcycloheptylamine and the like.

In one embodiment, the organic amine is preferably tertiary butyl amine.

The organic amine salts of compound of formula-1 of the present invention are very useful for the preparation of highly pure compound of formula-1.

The sixth aspect of the present invention provides a process for the preparation of organic amine salts of compound of formula-1, comprising of reacting the compound of formula-1 with a suitable organic amine in a suitable solvent to provide corresponding organic amine salt of compound of formula-1.

Wherein, the suitable organic amine is same as defined above; and the suitable solvent is selected from hydrocarbon solvents, ether solvents, ester solvents, polar-aprotic solvents, chloro solvents, ketone solvents, nitrile solvents, alcohol solvents, polar solvents and the like or mixtures thereof.

A preferred embodiment of the present invention provides a process for the preparation of tertiary butyl amine salt of compound of formula-1, comprising of reacting the compound of formula-1 with tertiary butyl amine in methyl tert-butyl ether or in a mixture of methyl tert-butyl ether and water to provide tertiary butyl amine salt of compound of formula-1.

An embodiment of the present invention provides the tertiary butyl amine salt of compound of formula-1 as a crystalline solid.

The crystalline tertiary butyl amine salt of compound of formula-1 of the present invention is characterized by its PXRD pattern having peaks at 7.8, 8.4, 12.1, 14.9, 17.0, 19.3, 20.6, 21.1, 21.7 and 22.4±0.2° of 2-theta values.

Figure 2:
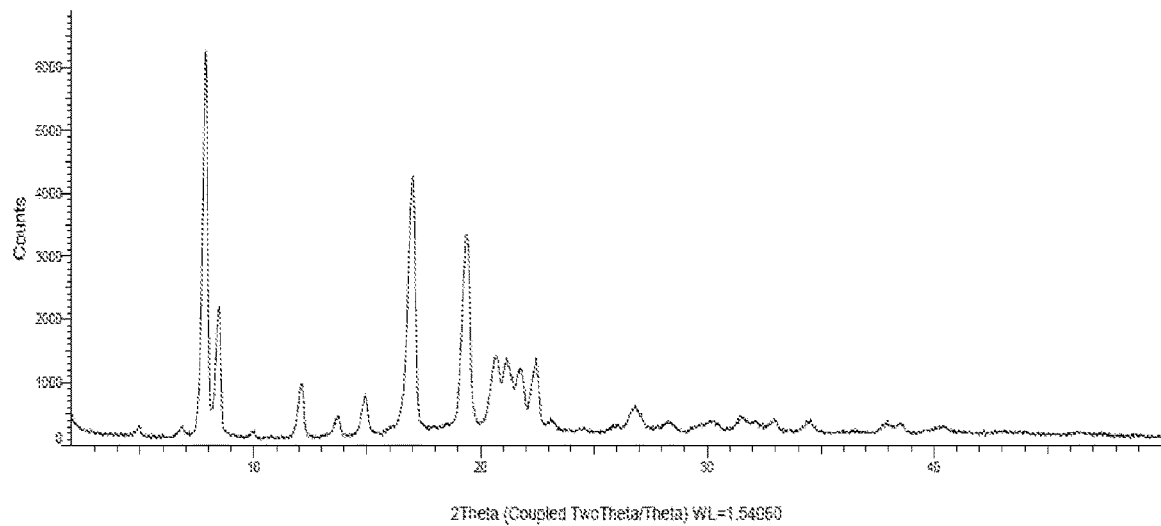
FIG. 2: Illustrates the powder X-Ray diffraction (PXRD) pattern of crystalline tertiary butyl amine salt of compound of formula-1.

In one embodiment of the present invention, the crystalline tertiary butyl amine salt of compound of formula-1 of the present invention is characterized by its PXRD pattern as illustrated in FIG. 2.

An embodiment of the present invention provides the use of above organic amine salts of compound of formula-1 for the preparation of pure compound of formula-1.

A preferred embodiment of the present invention provides the use of tertiary butyl amine salt of compound of formula-1 for the preparation of pure compound of formula-1.

The seventh aspect of the present invention provides a process for the purification of compound of formula-1, comprising of;
a) reacting the compound of formula-1 with a suitable organic amine in a suitable solvent,
b) optionally isolating the organic amine salt of compound of formula-1 from the reaction mixture,
c) treating the organic amine salt of compound of formula-1 with a suitable acid optionally in presence of a suitable solvent to provide pure compound of formula-1.

Wherein, in step-a) the suitable organic amine is same as defined above;

In step-c) the suitable acid is selected from hydrochloric acid, hydrobromic acid, sulfuric acid, nitric acid, phosphoric acid, formic acid, acetic acid, p-toluene sulfonic acid, methane sulfonic acid, trifluoroacetic acid and the like. In one embodiment, the suitable acid is preferably hydrochloric acid.

In step-a) to step-c) the suitable solvent is selected from hydrocarbon solvents, ether solvents, ester solvents, polar-aprotic solvents, chloro solvents, ketone solvents, nitrile solvents, alcohol solvents, polar solvents and the like or mixtures thereof.

WO2017093857A1 patent describes three crystalline polymorphic forms of compound of formula-1 namely form-1, form-2 and form-3.

The eighth aspect of the present invention provides a process for the preparation of crystalline form-2 of compound of formula-1. The said process comprising of;
a) dissolving the compound of formula-1 in a suitable solvent at a suitable temperature,
b) optionally filtering the solution,
c) combining the solution with a suitable anti-solvent at a suitable temperature to provide crystalline form-2 of compound of formula-1.

Wherein, in step-a) the suitable solvent is selected from alcohol solvents, polar-aprotic solvents, ester solvents, ketone solvents, ether solvents or mixtures thereof; and the suitable temperature ranges from 25° C. to 100° C.;

In step-c) the suitable anti-solvent is selected from water, hydrocarbon solvents or mixtures thereof; and the suitable temperature ranges from −60° C. to 60° C.

An embodiment of the present invention provides a process for the preparation of crystalline form-2 of compound of formula-1, comprising of;
a) dissolving the compound of formula-1 in methanol,
b) combining the solution with water to provide crystalline form-2 of compound of formula-1.

The other embodiment of the present invention provides a process for the preparation of crystalline form-2 of compound of formula-1, comprising of;
a) dissolving the compound of formula-1 in a mixture of methanol and dimethylsulfoxide,
b) combining the solution with water to provide crystalline form-2 of compound of formula-1.

Another embodiment of the present invention provides a process for the preparation of crystalline form-2 of compound of formula-1, comprising of;
a) dissolving the compound of formula-1 in a mixture of methanol and ethyl acetate,
b) optionally filtering the solution, c) combining the solution with a mixture of water and n-heptane to provide crystalline form-2 of compound of formula-1.

Figure 3:
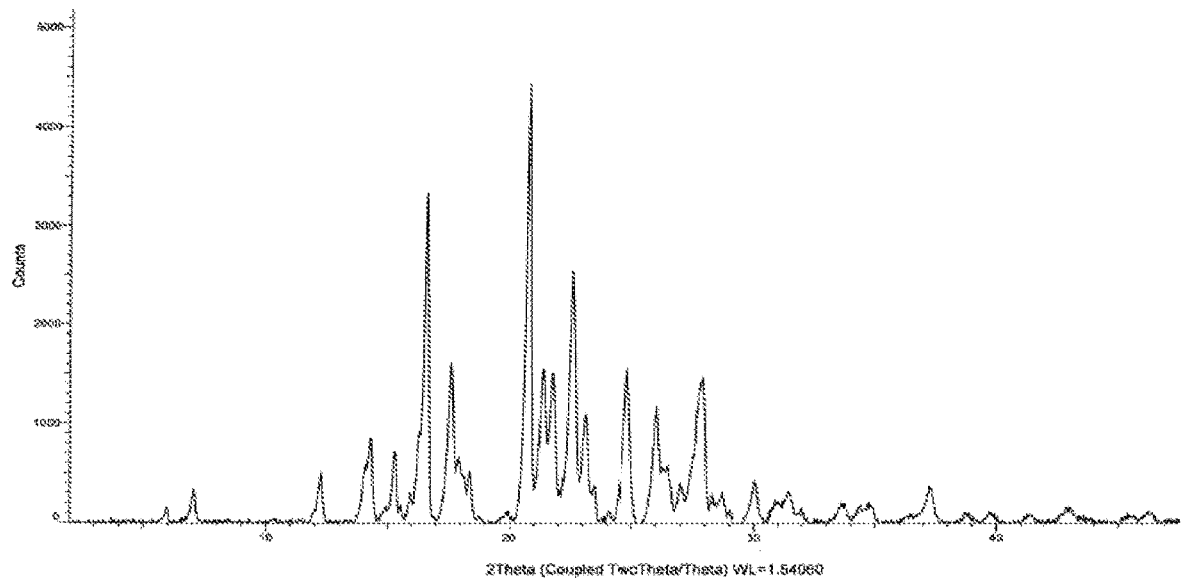
FIG. 3: Illustrates the PXRD pattern of crystalline 5-(4-cyanophenoxy)-1,3-dihydro-1-hydroxy-[2,1]-benzoxaborole (Formula-1) obtained according to example-7.

An embodiment of the present invention provides crystalline 5-(4-cyanophenoxy)-1,3-dihydro-1-hydroxy-[2,1]-benzoxaborole compound of formula-1. The said crystalline form is characterized by its PXRD pattern as shown in FIG. 3.

The other embodiment of the present invention provides a process for the preparation of crystalline compound of formula-1, comprising of;
a) adding a suitable solvent to compound of formula-1,
b) heating the reaction mixture to a suitable temperature,
c) cooling the reaction mixture to a suitable temperature,
d) filtering the solid and drying the material to provide crystalline compound of formula-1.

Wherein, in step-a) the suitable solvent is selected from hydrocarbon solvents;

In step-b) the suitable temperature ranges from 30-100° C.; and

In step-c) the suitable temperature ranges from 0-30° C.

Figure 4:
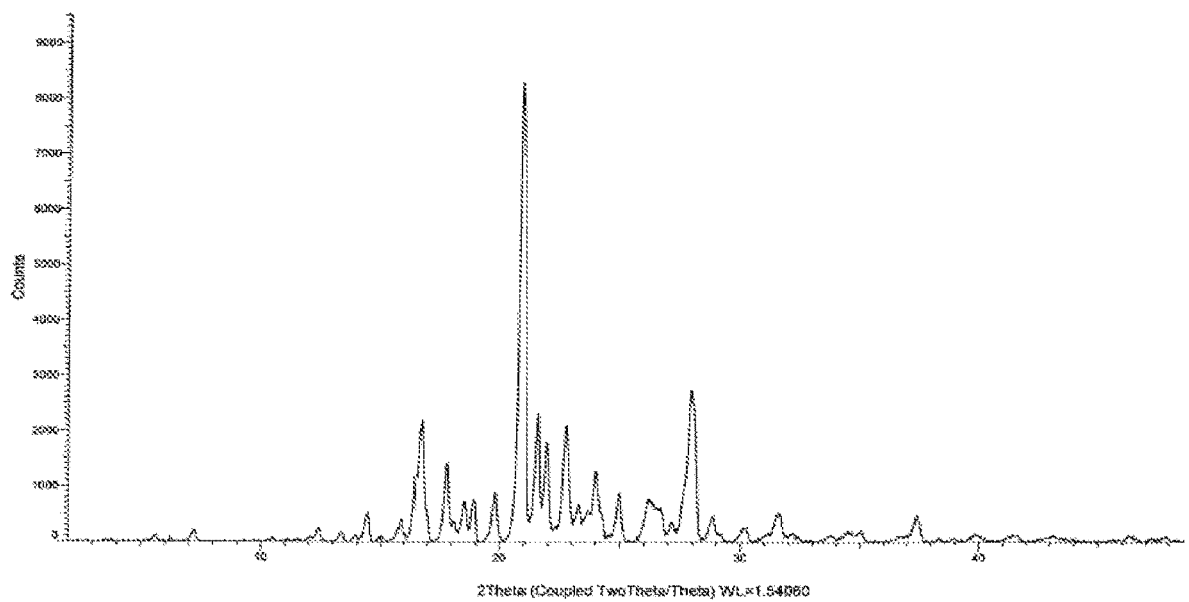
FIG. 4: Illustrates the PXRD pattern of crystalline 5-(4-cyanophenoxy)-1,3-dihydro-1-hydroxy-[2,1]-benzoxaborole (Formula-1) obtained according to example-8.

An embodiment of the present invention provides crystalline 5-(4-cyanophenoxy)-1,3-dihydro-1-hydroxy-[2,1]-benzoxaborole compound of formula-1. The said crystalline form is characterized by its PXRD pattern as shown in FIG. 4.

The other embodiment of the present invention provides a process for the preparation of crystalline compound of formula-1, comprising of;
a) slurrying the compound of formula-1 in a suitable solvent at a suitable temperature,
b) filtering the solid and drying the material to provide crystalline compound of formula-1.

Wherein, in step-a) the suitable solvent is selected from hydrocarbon solvents and the suitable temperature ranges from 0-30° C.

Figure 5:
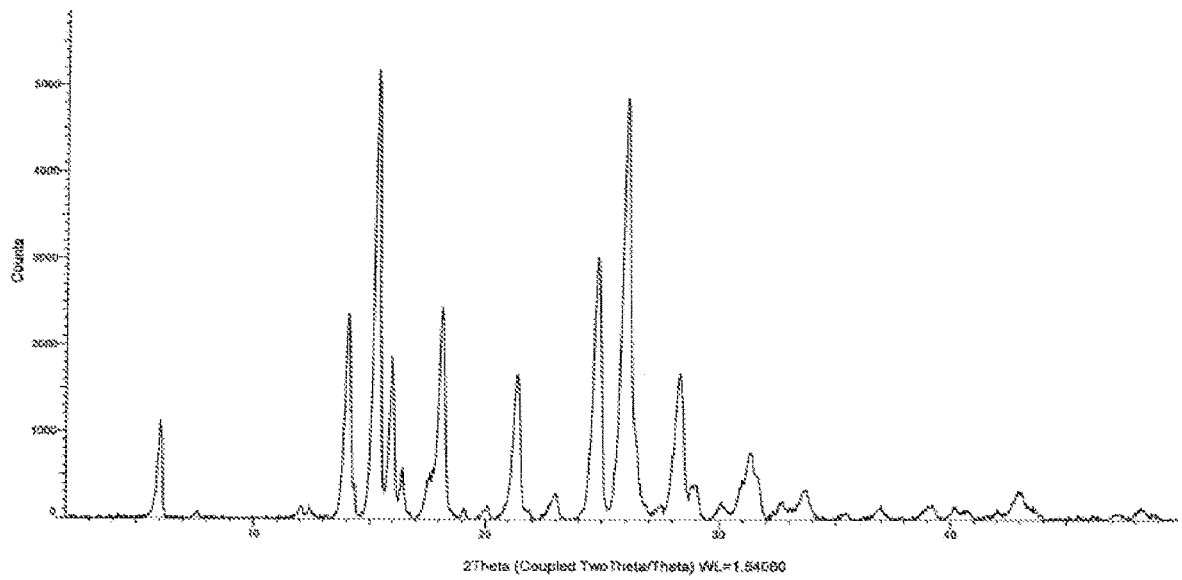
FIG. 5: Illustrates the PXRD pattern of crystalline 5-(4-cyanophenoxy)-1,3-dihydro-1-hydroxy-[2,1]-benzoxaborole (Formula-1) obtained according to example-9.

An embodiment of the present invention provides crystalline 5-(4-cyanophenoxy)-1,3-dihydro-1-hydroxy-[2,1]-benzoxaborole compound of formula-1. The said crystalline form is characterized by its PXRD pattern as shown in FIG. 5.

The other embodiment of the present invention provides a process for the preparation of crystalline compound of formula-1, comprising of;
a) adding a suitable solvent to compound of formula-1,
b) heating the reaction mixture to a suitable temperature,
c) optionally treating the reaction mixture with charcoal,
d) cooling the reaction mixture to a suitable temperature,
e) filtering the solid and drying the material to provide crystalline compound of formula-1.

Wherein, in step-a) the suitable solvent is selected from but not limited to alcohol solvents, chloro solvents, polar-aprotic solvents, nitrile solvents, ketone solvents, ether solvents, ester solvents or mixtures thereof;

In step-b) the suitable temperature ranges from 35-70° C.; and

In step-d) the suitable temperature ranges from 0-30° C.

The compound of formula-1 which is used as input in the above processes can be prepared by the process of the present invention or it can be prepared by any of the processes known in the art.

The crystalline polymorphs of compound of formula-1 of the present invention are useful for the preparation of various pharmaceutical compositions formulated in a manner suitable for the route of administration to be used where at least a portion of compound of formula-1 is present in the composition in particular polymorphic form mentioned.

An embodiment of the present invention provides pharmaceutical composition comprising any of the crystalline polymorphs of compound of formula-1 of the present invention and at least one pharmaceutically acceptable excipient.

Another embodiment of the present invention provides method of treating a condition or disease comprising administering to the patient a therapeutically effective amount of any of the crystalline polymorphs of compound of formula-1 of the present invention.

The compound of formula-1 produced by the process of the present invention is having particle size distribution of $D_{90}$ less than 500 μm, preferably less than 250 μm, more preferably less than 100 μm, most preferably less than 50 μm.

An embodiment of the present invention provides compound of formula-1 with particle size distribution of $D_{90}$ less than 20 μm, preferably less than 10 μm.

The compound of formula-1 produced by any of the processes of the present invention can be further micronized or milled to get desired particle size to achieve desired solubility profile based on different forms of pharmaceutical composition requirements. Techniques that may be used for particle size reduction includes but not limited to single or multi-stage micronization using cutting mills, pin/cage mills, hammer mills, jet mills, fluidized bed jet mills, ball mills and roller mills. Milling or micronization may be performed before drying or after drying of the product.

Particle Size Distribution (PSD) Method of Analysis

The particle size distribution analysis was carried out by using Malvern Mastersizer 3000 instrument.

PXRD Method of Analysis

The PXRD analysis of compounds of the present invention was carried out using BRUKER/D8 ADVANCE diffractometer using CuKα radiation of wavelength 1.5406A° and at a continuous scan speed of 0.03°/min.

HPLC Method of Analysis

The compound of formula-1 produced by the process of the present invention was analyzed by HPLC under the following conditions:

Apparatus: A liquid chromatograph equipped with variable wavelength UV detector; Column: Kromasil C18, 250×4.6 mm, 5.0 μm (Or) equivalent; Wavelength: 210 nm; Column temperature: 20° C.; Auto sampler temperature: 5° C.; Injection volume: 5 μL; Diluent: Acetonitrile (100%); Elution: Gradient; Buffer preparation: Accurately transfer 1000 mL of milli-Q-water into a suitable clean and dry beaker. Transfer accurately 1.0 mL of orthophosphoric acid (85%) into 1000 mL of Milli-Q-water and mix well. Filter this solution through 0.22 μm Durapore PVDF filter paper; Mobile phase-A: Buffer (100%); Mobile phase-B: Acetonitrile (100%); Sample concentration: 0.5 mg/mL.

The present invention is schematically represented as follows;

Scheme-I

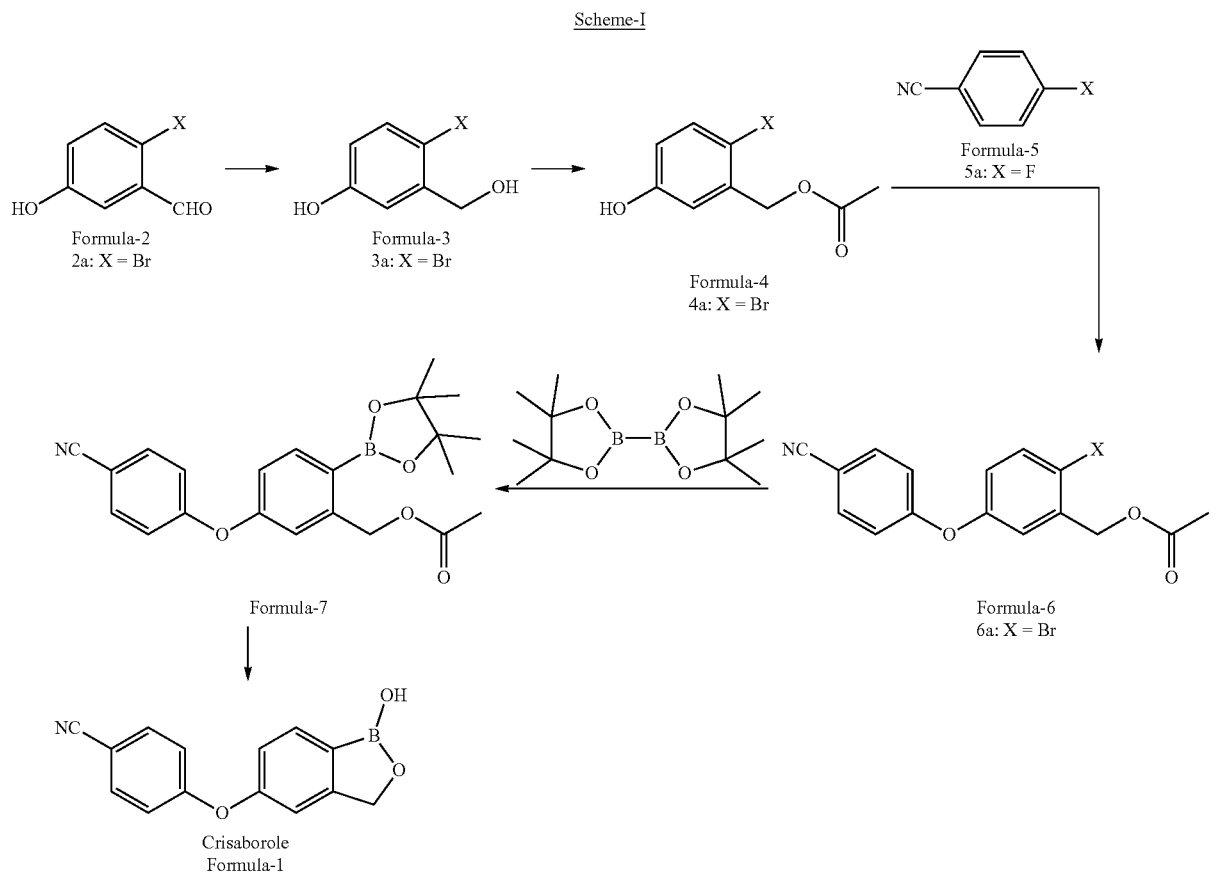

Wherein, 'X' represents halogen such as F, Cl, Br & I.

The best mode of carrying out the present invention is illustrated by the below mentioned examples. These examples are provided as illustration only and hence should not be construed as limitation to the scope of the invention.

EXAMPLES

Example-1: Preparation of 4-bromo-3-(hydroxymethyl)phenol (Formula-3a)

Sodium borohydride (9.4 gm) was slowly added to a pre-cooled mixture of 2-bromo-5-hydroxy benzaldehyde compound of formula-2a (100 gm) and tetrahydrofuran (300 ml) at 0-5° C. and stirred the reaction mixture for 2 hr at the same temperature. Acidified the reaction mixture with aqueous hydrochloric acid solution at 0-5° C. Raised the temperature of the reaction mixture to 25-30° C., ethyl acetate was added to it and stirred for 20 min at the same temperature. Both the organic and aqueous layers were separated and extracted the aqueous layer with ethyl acetate. Combined the organic layers and washed with water. Distilled off the solvent completely from the organic layer under reduced pressure and co-distilled with dichloromethane. Dichloromethane (300 ml) was added to the obtained compound at 25-30° C. and stirred the reaction mixture for 90 min at the same temperature. Filtered the solid, washed with dichloromethane and dried the material to get the title compound.

Yield: 91.82 gm; M.R.: 136.8-142.3° C.

Example-2: Preparation of 2-bromo-5-(4-cyanophenoxy)benzyl acetate (Formula-6a)

Triethylamine (74.7 gm) was added to a pre-cooled mixture of 4-bromo-3-(hydroxymethyl)phenol compound of formula-3a (100 gm) and ethyl acetate (400 ml) at 0-5° C. under nitrogen atmosphere. A solution of acetic anhydride (60 gm) in ethyl acetate (100 ml) was slowly added drop wise to the reaction mixture at 0-5° C. and stirred for 3 hr at the same temperature. Water (500 ml) was added to the reaction mixture at 0-5° C. Raised the temperature of the reaction mixture to 25-30° C. and stirred for 20 min at the same temperature. Both the organic and aqueous layers were separated and the aqueous layer was extracted with ethyl acetate. Combined the organic layers and washed with aqueous sodium bicarbonate solution followed by with aqueous sodium chloride solution. Distilled off the solvent completely from the organic layer under reduced pressure. Dimethylsulfoxide (500 ml), potassium carbonate (102.1 gm) and 4-fluorobenzonitrile compound of formula-5a (71.5 gm) were added to the obtained compound at 25-30° C. Heated the reaction mixture to 90-95° C. and stirred for 5 hr at the same temperature. Cooled the reaction mixture to 25-30° C., acetic anhydride (25 gm) was added to it and stirred for 1 hr at the same temperature. Cooled the reaction mixture to 0-5° C. and acidified it with aqueous ortho phosphoric acid solution at the same temperature. Raised the temperature of the reaction mixture to 25-30° C. and stirred for 1 hr at the same temperature. Filtered the solid and washed with water. Ethyl acetate and water were added to the obtained compound at 25-30° C. and stirred the reaction mixture for 20 min at the same temperature. Both the organic and aqueous layers were separated and extracted the aqueous layer with ethyl acetate. Combined the organic layers and washed with aqueous sodium chloride solution. Charcoal (10 gm) was added to the organic layer at 25-30° C. Heated the reaction mixture to 60-65° C. and stirred for 1 hr at the same temperature. Filtered the reaction mixture through hyflow bed and washed the hyflow bed with ethyl acetate. Distilled off the solvent completely from the filtrate under reduced pressure and co-distilled with isopropyl alcohol. Isopropyl alcohol (700 ml) was added to the obtained compound at 25-30° C. Heated the reaction mixture to 60-65° C. and stirred for 1 hr at the same temperature. Cooled the reaction mixture to 0-5° C. and stirred for 90 min at the same temperature. Filtered the solid, washed with cyclohexane and dried to get the title compound. The PXRD pattern of the obtained compound is shown in FIG. 1.
Yield: 127.9 gm; M.R.: 79-82° C.

Example-3: Preparation of Compound of Formula-1

Bis(pinacolato)diboron (275 gm) and potassium acetate (283.45 gm) were added to a mixture of 2-bromo-5-(4-cyanophenoxy)benzyl acetate compound of formula-6a (250 gm) and 1,4-dioxane (2.5 Lt) at 25-30° C. under nitrogen atmosphere. Purged the reaction mixture with nitrogen gas for 30 min. Pd(dppf)Cl$_2$ (17.67 gm) was added to the reaction mixture at 25-30° C. and purged the reaction mixture with nitrogen gas for 15 min. Heated the reaction mixture to 85-90° C. and stirred for 3 hr at the same temperature. Cooled the reaction mixture to 25-30° C. Filtered the reaction mixture and washed with 1,4-dioxane. Hydrochloric acid solution (750 ml of hydrochloric acid in 500 ml of water) was added to the reaction mixture at 25-30° C. Heated the reaction mixture to 85-90° C. and stirred for 4 hr at the same temperature. Cooled the reaction mixture to 25-30° C. Ethyl acetate and aqueous sodium chloride solution were added to the reaction mixture at 25-30° C. and stirred for 30 min at the same temperature. Both the organic and aqueous layers were separated and aqueous layer was extracted with ethyl acetate. Combined the organic layers and washed with aqueous sodium chloride solution. Distilled off the solvent completely from the organic layer under reduced pressure. Ethyl acetate and aqueous sodium chloride solution were added to the obtained compound at 25-30° C. and stirred the reaction mixture for 15 min at the same temperature. Both the organic and aqueous layers were separated. Charcoal (50 gm) was added to the organic layer at 25-30° C. Heated the reaction mixture to 65-70° C. and stirred for 1 hr at the same temperature. Filtered the reaction mixture through hyflow bed and washed the hyflow bed with ethyl acetate. Distilled off the solvent completely from the filtrate under reduced pressure and co-distilled with n-heptane followed by with methanol under reduced pressure. Methanol (250 ml) was added to the obtained compound at 25-30° C. and stirred the reaction mixture for 1 hr at the same temperature. Filtered the solid and washed with methanol. Methanol (1 Lt) was added to the obtained compound at 25-30° C. Heated the reaction mixture to 65-70° C. and stirred for 1 hr at the same temperature. Cooled the reaction mixture to 25-30° C. and stirred for 90 min at the same temperature. Filtered the solid, washed with methanol and dried the material to get the title compound.
Yield: 100.0 gm.

Example-4: Purification of Compound of Formula-1

Step-a): Tertiary butyl amine (40 ml) was added to a mixture of compound of formula-1 (20 gm) and methyl tert-butyl ether (60 ml) at 25-30° C. and stirred the reaction mixture for 1 hr at the same temperature. Water (20 ml) and methyl tert-butyl ether (20 ml) were added to the reaction mixture at 25-30° C. and stirred for 1 hr at the same temperature. Filtered the solid, washed with methyl tert-butyl ether and dried the material to get the tertiary butyl amine salt of compound of formula-1.
The PXRD pattern of the obtained compound is shown in FIG. 2.
Step-b): Methanol (40 ml) was added to the compound obtained in step-a) at 25-30° C. Cooled the reaction mixture to 0-5° C. and aqueous hydrochloric acid solution (10 ml of hydrochloric acid in 70 ml water) was added to it at the same temperature. Raised the temperature of the reaction mixture to 25-30° C. and stirred for 1 hr at the same temperature. Filtered the solid, washed with water and dried the material to get the title compound. The PXRD pattern of the obtained compound is similar to the PXRD pattern of crystalline form-2 described in WO2017093857A1.
Yield: 6.0 gm.

Example-5: Purification of Compound of Formula-1

A mixture of compound of formula-1 (200 gm) and ethyl acetate (2 Lt) was stirred for 20 min at 25-30° C. Filtered the reaction mixture to make it particle free. Distilled off the solvent completely from the filtrate under reduced pressure and co-distilled with methanol. Methanol (2 Lt) was added to the obtained compound at 25-30° C. Heated the reaction mixture to 65-70° C. and stirred for 45 min at the same temperature. The obtained solution was added to pre-cooled water (6 Lt) at 0-5° C. and stirred the reaction mixture for 1 hr at the same temperature. Filtered the solid, washed with water and dried to get the title compound. The PXRD pattern of the obtained compound is similar to the PXRD pattern of crystalline form-2 described in WO2017093857A1.
Yield: 165.0 gm; Purity by HPLC: 99.96%.
Particle size distribution: D(0.1) is 1.79 μm; D(0.5) is 4.05 μm; D(0.9) is 9.52 μm.

Example-6: Purification of Compound of Formula-1

Methanol (400 ml) and dimethylsulfoxide (300 ml) were added to compound of formula-1 (100 gm) at 25-30° C. and stirred the reaction mixture for 1 hr at the same temperature. Filtered the reaction mixture to make it particle free. The obtained filtrate was added to pre-cooled water (2.1 Lt) at 0-5° C. and stirred the reaction mixture for 1 hr at the same temperature. Filtered the precipitated solid, washed with water and dried the material to get the title compound. The PXRD pattern of the obtained compound is similar to the PXRD pattern of crystalline form-2 described in WO2017093857A1.
Yield: 83.0 gm.

Example-7: Preparation of Crystalline Compound of Formula-1

A mixture of compound of formula-1 (1.5 gm) and ethyl acetate (24 ml) was stirred for 10 min at 25-30° C. Distilled off the solvent completely from the reaction mixture and co-distilled with n-heptane. 12 ml of n-heptane was added to the obtained compound. Heated the reaction mixture to 70-75° C. and stirred for 2 hr at the same temperature. Cooled the reaction mixture to 25-30° C. and stirred for 90 min at the same temperature. Filtered the solid, washed with n-heptane and dried the material to get the title compound. The PXRD pattern of the obtained compound is shown in FIG. 3. Yield: 1.1 gm.

Example-8: Preparation of Crystalline Compound of Formula-1

A mixture of compound of formula-1 (5 gm) and ethyl acetate (50 ml) was stirred for 20 min at 25-30° C. Filtered the reaction mixture and washed with ethyl acetate. Distilled off the solvent completely from the filtrate and co-distilled with n-heptane. 50 ml of n-heptane was added to the obtained compound at 25-30° C. and stirred the reaction mixture for 2 hr at the same temperature. Filtered the solid, washed with n-heptane and dried the material to get the title compound. The PXRD pattern of the obtained compound is shown in FIG. 4.
Yield: 4.5 gm.

Example-9: Preparation of Crystalline Compound of Formula-1

A mixture of compound of formula-1 (54 gm) and methanol (432 ml) was heated to 60-65° C. and stirred for 30 min at the same temperature. Charcoal (5.4 gm) was added to the reaction mixture at 60-65° C. and stirred for 90 min at the same temperature. Filtered the reaction mixture through hyflow bed and washed the hyflow bed with methanol. Cooled the filtrate to 25-30° C. and stirred for 90 min at the same temperature. Filtered the solid, washed with methanol and then dried the material to get the title compound. The PXRD pattern of the obtained compound is shown in FIG. 5. Yield: 37.0 gm.

Example-10: Preparation of Crystalline Compound of Formula-1

Figure 6:
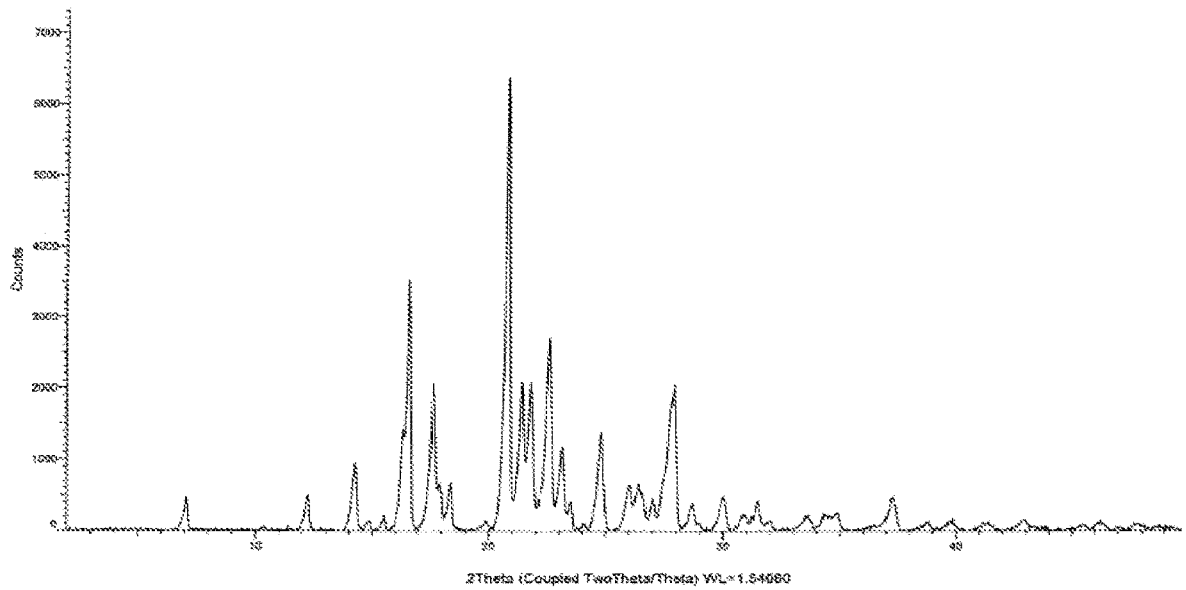
FIG. 6: Illustrates the PXRD pattern of crystalline 5-(4-cyanophenoxy)-1,3-dihydro-1-hydroxy-[2,1]-benzoxaborole (Formula-1) obtained according to example-10.

A mixture of compound of formula-1 (2 gm), ethyl acetate (80 ml) and cyclohexane (80 ml) was stirred for 10 min at 25-30° C. Distilled off the solvent completely from the reaction mixture and co-distilled with cyclohexane. Cyclohexane (16 ml) was added to the obtained compound. Heated the reaction mixture to 70-75° C. and stirred for 2 hr at the same temperature. Cooled the reaction mixture to 25-30° C. and stirred for 90 min at the same temperature. Filtered the solid, washed with cyclohexane and dried to get the title compound. The PXRD pattern of the obtained compound is shown in FIG. 6. Yield: 1.7 gm.

Example-11: Preparation of Crystalline Compound of Formula-1

A mixture of compound of formula-1 (2 gm), ethyl acetate (300 ml) and cyclohexane (300 ml) was stirred for 10 min at 25-30° C. Distilled off the solvent completely from the reaction mixture and co-distilled with n-hexane. 16 ml of n-hexane was added to the obtained compound. Heated the reaction mixture to 70-75° C. and stirred for 2 hr at the same temperature. Cooled the reaction mixture to 25-30° C. and stirred for 90 min at the same temperature. Filtered the solid, washed with n-hexane and dried the material to get the title compound.
The PXRD pattern of the obtained compound is similar to FIG. 6.
Yield: 1.5 gm.

Example-12: Preparation of Crystalline Form-2 of Compound of Formula-1

Compound of formula-1 (5 gm) was dissolved in a 1:1 mixture of methanol and ethyl acetate (50 ml) at 25-30° C. Filtered the solution to make it particle free. The obtained filtrate was added to a pre-cooled mixture of n-heptane (100 ml) and water (100 ml) at 0-5° C. and stirred the reaction mixture for 15 min at the same temperature. Filtered the precipitated solid and dried the material to get the title compound.
The PXRD pattern of the obtained compound is similar to the PXRD pattern of crystalline form-2 described in WO2017093857A1.
Yield: 3.9 gm.

Example-13: Preparation of Crystalline Form-2 of Compound of Formula-1

Compound of formula-1 (50 gm) was dissolved in a 1:1 mixture of methanol and ethyl acetate (500 ml) at 25-30° C. Filtered the solution to make it particle free. The obtained filtrate was slowly added to a pre-cooled mixture of n-heptane (1 Lt) and water (1 Lt) at 0-5° C. and stirred the reaction mixture for 15 min at the same temperature. Filtered the precipitated solid and dried the material to get the title compound.
The PXRD pattern of the obtained compound is similar to the PXRD pattern of crystalline form-2 described in WO2017093857A1.
Yield: 40.0 gm.

We claim:
1. A process for the preparation of 5-(4-cyanophenoxy)-1,3-dihydro-1-hydroxy-[2,1]-benzoxaborole compound of formula-1, comprising;

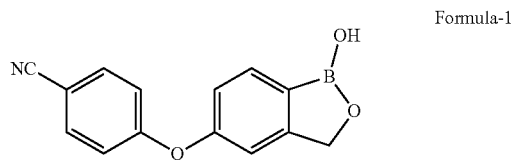 [SMILES: N#Cc1ccc(Oc2ccc3c(c2)COB3O)cc1]

Formula-1 a) reacting 2-halo-5-hydroxybenzyl acetate compound of general formula-4

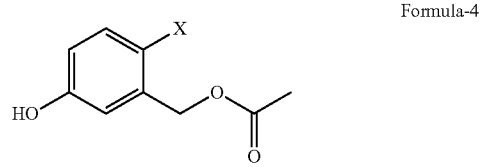

Formula-4 with 4-halobenzonitrile compound of general formula-5

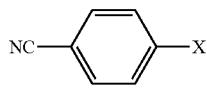

Formula-5 wherein, 'X' represents halogens such as F, Cl, Br & I; to obtain 2-halo-5-(4-cyanophenoxy)benzyl acetate compound of general formula-6, and

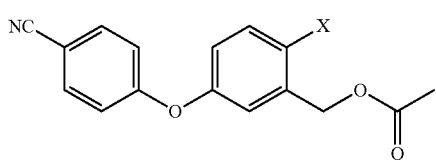

Formula-6 b) converting the compound of general formula-6 into compound of formula-1.

2. The process according to claim 1, comprising reacting compound of general formula-6 with bis(pinacolato)diboron compound having the following formula

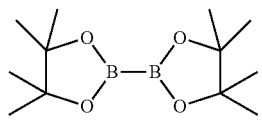

in presence of a palladium catalyst and a base in a solvent to provide 5-(4-cyanophenoxy)-2-(4,4,5,5-tetramethyl-1,3,2-dioxaborolan-2-yl)benzyl acetate compound of formula-7, Formula-7

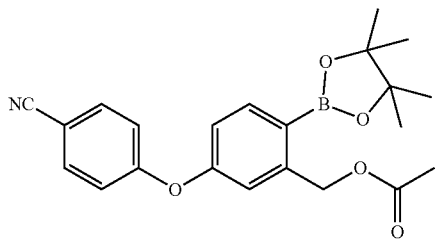

and treating compound of formula-7 with an acid optionally in presence of a solvent to provide compound of formula-1.

3. The process according to claim 1, wherein, the reaction in step-a) is carried out in presence of a base selected from inorganic bases, organic bases or mixtures thereof in a solvent selected from the group consisting of hydrocarbon solvents, ether solvents, ester solvents, polar-aprotic solvents, chloro solvents, ketone solvents, nitrile solvents, alcohol solvents, polar solvents, and mixtures thereof.

4. The process according to claim 2, wherein the palladium catalyst is selected from the group consisting of palladium(II) acetate, palladium(II) acetoacetonate, palladium chloride ($PdCl_2$), tetrakis(triphenyl phosphine)palladium, dichlorobis(triphenylphosphine) palladium, [1,1'-bis(diphenylphosphino) ferrocene] dichloro palladium(II) [$Pd(dppf)Cl_2$], and combinations thereof; and wherein the reaction can be carried out optionally in presence of a ligand such as triphenylphosphine, tri(o-tolyl)phosphine, tricyclohexylphosphine combinations thereof;

a base is selected from inorganic bases, organic bases or mixtures thereof;

an acid is preferably hydrochloric acid; and a solvent is selected from the group consisting of hydrocarbon solvents, ether solvents, ester solvents, polar-aprotic solvents, chloro solvents, ketone solvents, nitrile solvents, alcohol solvents, polar solvents, and mixtures thereof.

5. The process according to claim 1, wherein the 2-halo-5-hydroxybenzyl acetate compound of general formula-4

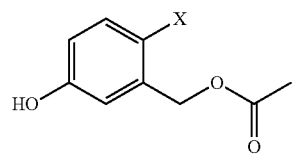

Formula-4 wherein, 'X' represents halogens such as F, Cl, Br & I; is prepared by reacting 4-halo-3-(hydroxymethyl)phenol compound of general formula-3

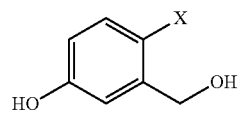

Formula-3 with an acetylating agent, optionally in presence of a base in a solvent.

6. The process according to claim 5, wherein the acetylating agent is selected from the group consisting of acetic anhydride, acetyl chloride, acetic acid and mixtures thereof; the base is selected from organic bases; and the solvent is selected from the group consisting of hydrocarbon solvents, ether solvents, ester solvents, polar-aprotic solvents, chloro solvents, ketone solvents, nitrile solvents, alcohol solvents, polar solvents, and mixtures thereof.

7. The process according to claim 2 further comprising purification of compound of formula-1, comprising:

a) reacting the compound of formula-1 with an organic amine in a solvent, b) optionally isolating the organic amine salt of compound of formula-1 from the reaction mixture, and c) treating the organic amine salt of compound of formula-1 with an acid optionally in presence of a solvent to provide pure compound of formula-1.

8. The process according to claim 7, wherein, the "organic amine" is selected from methyl amine, ethyl amine, n-propyl amine, isopropyl amine, n-butyl amine, iso-butyl amine, tertiary butyl amine, octyl amine, 2-ethyl hexylamine, benzyl amine, α-methyl-benzylamine, phenyl ethylamine, dibenzylamine, N-methylbenzylamine, N,N-dimethylbenzylamine, N,N-diethyl benzyl amine, N-ethyl-N-methylbenzylamine, tribenzyl amine, cyclopentyl amine, cyclohexyl amine, cycloheptylamine, N-methylcyclopentylamine, N-ethyl cyclohexyl amine, N-ethyl cycloheptylamine, dicyclohexyl amine, N,N-dimethyl cyclo pentylamine, N,N-dimethyl cyclohexylamine, N,N-diethylcycloheptylamine and the like;

the acid is selected from hydrochloric acid, hydrobromic acid, sulfuric acid, nitric acid, phosphoric acid, formic acid, acetic acid, p-toluene sulfonic acid, methane sulfonic acid, trifluoroacetic acid and the like;

the solvent is selected from hydrocarbon solvents, ether solvents, ester solvents, polar-aprotic solvents, chloro solvents, ketone solvents, nitrile solvents, alcohol solvents, polar solvents and the like or mixtures thereof.

9. The process according to claim 7, wherein the organic amine salt is preferably tertiary butyl amine salt.

10. The process according to claim 9, wherein the tertiary butyl amine salt of compound of formula-1 is obtained as a crystalline solid.

* * * * *